United States Patent [19]

Mueller

[11] 4,410,742
[45] Oct. 18, 1983

[54] ORGANOMAGNESIUM ALKOXIDES AND METHOD FOR MAKING THE SAME

[75] Inventor: Karl H. Mueller, Werne, both of Fed. Rep. of Germany

[73] Assignees: Schering AG, Berlin and Bergkamen, Fed. Rep. of Germany; Ulrich Schroeer, Kamen-Methler

[21] Appl. No.: 384,787

[22] Filed: Jun. 4, 1982

Related U.S. Application Data

[63] Continuation-in-part of Ser. No. 192,104, Sep. 29, 1980, abandoned.

[30] Foreign Application Priority Data

Oct. 10, 1979 [DE] Fed. Rep. of Germany ....... 2941048

[51] Int. Cl.$^3$ ............................................. C07C 29/68
[52] U.S. Cl. .................................... 568/851; 526/183
[58] Field of Search ........................................ 568/851

[56] References Cited

U.S. PATENT DOCUMENTS 3,755,478  8/1973  Kamienski .................... 260/665 R
4,133,824  1/1979  Malpass et al. ................. 252/431 R
4,159,965  7/1979  Sakurai et al. .................. 252/431 R

FOREIGN PATENT DOCUMENTS 955806  4/1964  United Kingdom .

OTHER PUBLICATIONS

Ashby, J. Amer. Chem. Soc. 97, 3162–3171 (1975).
Coates, Rec. of Chem. Progr. 28, 3–23 (1967).
Bryce-Smith et al., J. Chem. Soc. (1964), 2483–2485.
Coates et al. J. Chem. Soc.(A) (1968) 1118–1125.
House et al., J. Org. Chem. 28, 348–355 (1963).
Tsuruta et al. Makromol. Chem. 103, 164–174 (1967).
Hollander et al., Bl. Soc. Chim. Belg. 74, 71–89 (1965).
Cowan et al. J. Org. Chem. 28, 204–206 (1963).
House et al. J. Org. Chem. 28, 355–360 (1963).
Malpass et al. J. Organometallic Chem. 93, 1–8 (1975).

Primary Examiner—J. E. Evans
Attorney, Agent, or Firm—Curtis, Morris & Safford

[57] ABSTRACT

What are disclosed are a method for making halogen-free organomagnesium alkoxides of the formula $$R^1{}_aR^2{}_bMg(OR^3)_c(OR^4)_c,$$

wherein $R^1$ and $R^2$ are phenyl or alkyl, $R^3$ and $R^4$ are alkyl, and wherein $(a+b)=(c+d)=1$, by reacting $$(R^1{}_aR^2{}_b)_2 Mg$$

with $Mg [(OR^3)_c(OR^4)_d]_2$, halogen-free organomagnesium alkoxides made by this method, and stable solutions of such organomagnesium alkoxides in an inert hydrocarbon solvent.

4 Claims, No Drawings

ORGANOMAGNESIUM ALKOXIDES AND METHOD FOR MAKING THE SAME

This application is a continuation-in-part of application Ser. No. 192,104 filed Sept. 29, 1980 now abandoned.

The present invention relates to organomagnesium alkoxides and to methods for making the same.

Alkylmagnesium alkoxides are a known type of compound. Different routes to their preparation are known, all of which, however, are burdened with disadvantages.

Houben-Weyl, Vol. XIII/2a gives a brief overview. Thus, for the reaction between magnesium, alkyl halides, and alcohol, an additional molecule of alkyl halide is employed which results in the formation of an alkane:

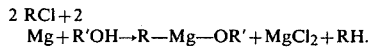

$$2\ RCl + 2\ Mg + R'OH \rightarrow R-Mg-OR' + MgCl_2 + RH.$$

The compounds obtained are associated and have been partially investigated [J. Amer. Chem. Soc. 97, 3162 (1975); Rec. of Chem. Progr. 28, 3 (1967)]. For the sake of simplicity they are represented in the present specification and claims as monomers.

Starting from ethereal Grignard solutions, ether is always first introduced. This can disturb further use considerably and the removal of the ether is an expensive operating step [Rec. of Chem. Prog. 28, 21 (1967)].

The reaction of Grignard compounds with alkali metal alcoholates outside of the undesired ether introduces another foreign metal that then again must be completely removed:

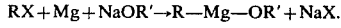

$$RX + Mg + NaOR' \rightarrow R-Mg-OR' + NaX.$$

The precipitates which are formed in this reaction often include considerable amounts of the desired product, which leads to a reduction in yields. Nevertheless, the desired products contain not inconsiderable amounts of the foreign metal.

If the alcoholate is prepared first in order to save the use of excess alkyl halide, the alcoholate must be available in highly diluted suspension because it is insoluble or difficulty soluble in almost all solvents. During the reactions of further magnesium with alkyl halide carried out in the suspensions, disruptive side reactions occur according to:

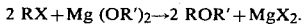

$$2\ RX + Mg(OR')_2 \rightarrow 2\ ROR' + MgX_2.$$

[Chem. Ber. 44, 2847 (1911)]. Also, alkylmagnesium and alkoxymagnesium materials are trapped in the magnesium chloride. Both phenomena lead to considerable loss of yield.

Three further methods require the destruction of alkylmagnesium compounds which must first be laboriously prepared and these methods are comparable in their disadvantages to the method first mentioned herein:

1. reaction of 2 mols of Grignard reagent or of 1 mol of dialkylmagnesium with 1 mol of alcohol [J. Chem. Soc. (1964) 2482; J. Chem. Soc. (A) (1968) 1118];
2. addition of alkylmagnesium compounds to carbonyl compounds or epoxides [J. Org. Chem. 28, 348 (1963); Makromol. Chem. 103, 164 (1967)]; and
3. partial oxidation of dialkylmagnesium compounds [Bl. Soc. chim. Belg. 74, 71 (1965)].

It has been indicated that ethereal alkylmagnesium alkoxide solutions [J. Org. Chem. 28, 204 (1963); J. Org. Chem. 28, 355 (1963)] can participate in an equilibrium of the Schlenk type:

$$2\ RMgOR' \rightleftharpoons MgR_2 + Mg(OR')_2.$$

However, it turns out that the alkylmagnesium alkoxides supposedly produced from dialkylmagnesium and dialkoxymagnesium in fact comprise a mixture of dialkylmagnesium and dialkoxymagnesium.

According to Malpass et al. U.S. Pat. No. 4,133,824, complexes of the formula $(R_2Mg)_m[(RO)_2Mg]_n$ are obtained by a process in which magnesium is reacted with an organohalide of the formula RX and, during or after the reaction, magnesium alkoxide is added to the reaction product. Thus, according to Example II of this patent, the total product mixture of the Grignard reaction of Example I is reacted with magnesium ethoxide allegedly to form butylmagnesium ethoxide in a 29 percent yield. In fact, however, since the reaction product of Example I of the Malpass et al. patent contains not only $(n-Bu)_2Mg$, which is insoluble in the hydrocarbon reaction medium, but also precipitated contaminants containing chloride bound to magnesium, a more complex chloride-containing product is obtained when the product mixture of Example I of the patent is reacted further in Example II with magnesium ethoxide. This complex product, containing chloride, is not $(Bu)_2Mg \cdot Mg(OEt)_2$ as alleged in the patent.

It has now been found that organomagnesium alkoxides which are free of halogen and are soluble in hydrocarbons can be prepared in a very simple process with high yields if magnesium alkyls soluble in hydrocarbons are reacted with magnesium dialkoxides in a mol ratio of 1:1. Since the synthetic method taught and claimed herein expressly employs a magnesium dialkyl starting material which is soluble in hydrocarbons, $(n-Bu)_2Mg$ is excluded from the method: this compound is insoluble in hydrocarbons [cf. Malpass et al., J. Organometallic Chem. 93, 1 (1975)] as is evident also from Example I of the Malpass et al. patent which unequivocally asserts "the presence of no metal alkyl [$(n-Bu)_2Mg$] in the [reaction] solution."

Freedom of the product from halogen is of importance since solutions of halogen-containing materials are unstable and their content varies with time. The usefulness of such solutions for the preparation of Ziegler catalysts is, thus, considerably impaired. Halogen-free products are prepared using the method of the present invention providing that care is taken that the starting materials, particularly the dialkylmagnesium reagent, is halogen-free.

A feature of the invention is, thus, a method for the preparation of halogen-free organomagnesium alkoxides, soluble in hydrocarbons of the formula

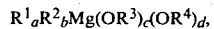

$$R^1_a R^2_b Mg(OR^3)_c (OR^4)_d,$$

wherein $R^1$ and $R^2$ are the same or different and are phenyl or alkyl having 1 to 12 carbon atoms, preferably 4 to 8 carbon atoms, $R^3$ and $R^4$ are the same or different and are alkyl having 2 to 6 carbon atoms, preferably 2 to 4 carbon atoms, and wherein $(a+b)$ as well as $(c+d)$ are equal to 1.

According to the method, soluble diorganomagnesium compounds of the formula $$[R^1{}_aR^2{}_b]_2Mg$$

are reacted at temperatures of about 50° to about 160° C. with compounds of the formula $$Mg[(OR^3)_c(OR^4)_d]_2.$$

Preferably, the reaction is carried out from about 80° to about 120° C.

A further feature of the invention are halogen-free hydrocarbon-soluble compounds of the formula $$R^1{}_aR^2{}_bMg(OR^3)_c(OR^4)_d$$

in which $R^1$ is butyl and $R^2$ is octyl. Particularly preferred are compounds with a butyl:octyl ratio of 3:1.

Preferred compounds are those in which $R^3$ and $R^4$ are ethyl and/or i-propyl, particularly the compound $$Bu_{0.75}Oc_{0.25}Mg(OEt)_{0.8}(OiPr)_{0.2}.$$

A further feature of the invention are stable solutions of the aforementioned compounds in inert hydrocarbons.

Exactly defined alkylmagnesium alkoxides, or solutions thereof in inert organic solvents, can be prepared in very high, mostly quantitative, yields: Further, it is possible to carry out the reaction with excess amounts of dialkylmagnesium or diarylmagnesium if this excess is desired in the final product.

The individual components are mixed in the desired ratio and the desired end product is formed after a short reaction time at temperatures of 50°–160° C., preferably 80°–120° C.

Diorganomagnesium compounds and magnesium dialcoholates are commercially available compounds which can be used as such. Suitable dialkylmagnesium compounds, soluble in hydrocarbons, are those, for example, with branched alkyl groups, such as di-sec.-butylmagnesium or butyl-sec.-butylmagnesium. Further, dialkylmagnesium compounds which contain ether or other complexformers such as aluminum alkyls in an amount from 1 to 10 mol percent can be used.

Magnesium dialkyls of this type can be prepared, for example, according to U.S. Pat. No. 3,755,478, German Pat. No. 2,027,327, or British Pat. No. 955,806.

The starting compounds can be used as individual compounds, as mixtures of individual compounds, or as mixed diorganomagnesium compounds.

The magnesium dialkoxides, which are per se solid and can scarcely be brought into solution, dissolve rapidly and when the most extremely pure starting compounds are used no residue remains. In the reactions with diorganomagnesium solutions according to the invention, clear solutions of the end product are formed, which solutions can be obtained as low viscosity strongly concentrated solutions or, if they contain large amounts of branched alkoxide groups on an alpha-carbon atom, can even be obtained concentrated in liquid form.

The products prepared according to the present invention—also those having short chains—are soluble in inert polar and non-polar solvents.

This provides great advantages in their availability and in their transport when contrasted with magnesium dialkoxides and magnesium dialkyl.

In addition to use as alkylating agents, the compounds prepared according to the present invention can be used as catalysts or as catalyst components for polymerization reactions.

Catalysts of this type are, for example, suitable for the polymerization of vinyl and allyl compounds, lactones, lactams, alpha-olefins, particularly ethylene and propylene, of dienes, particularly butadiene and isoprene, of epoxides, aldehydes, pyrrol derivatives, inter alia.

Depending on the nature and amount of additional catalysts compounds, catalysts having stereospecificity and efficacy can be prepared, e.g. Ziegler-type catalysts with titanium compounds.

A better understanding of the present invention and of its many advantages will be had by referring to the following specific Examples, given by way of illustration.

EXAMPLE 1

112.1 g of a solution of $Bu_{1.5}Oc_{0.5}Mg$ in an isononane mixture, having a magnesium content of 2.94 percent by weight—corresponding to 1.36 mol of dialkylmagnesium, an isopropylate content of 0.14 percent by weight, and an Al content of 0.08 percent by weight, were introduced into a vessel and 19.35 g of solid magnesium isopropylate were trickled in with stirring. The batch was heated for one hour at 120° C., whereupon the magnesium isopropylate went completely into solution.

The brownish solution was freed of solvent. An oil remained in a yield of 42 g, corresponding to 100 percent of theory.

Mg-content: 15.60 percent by weight (theory: 15.75%)

Mg-O-content: 7.83 percent by weight (theory: 7.88%)

Al-content: 0.19 percent by weight.

The oil had a viscosity of 89 centiStokes at 20° C., its density was 0.92 g cm$^{-3}$ at 24° C. The oil dissolves in all commonly used inert solvents.

EXAMPLE 2

214.6 g of an 18.67 percent solution of $Bu_{1.5}Oc_{0.5}Mg$ in isononane (0.241 mol of $R_2Mg$), having a diethylether content of less than 0.003 percent by weight, was combined with 27.5 g of Mg ethylate (0.241 mol) and kept at boiling temperature for one hour. A small amount of a gray-black precipitate was centrifuged off. The precipitate was washed with 20 ml of isononane and centrifuged again. The purified centrifugate had a viscosity of 1.87 centiStokes at 20° C.

The Mg content of the solution was 4.56 percent by weight (equal to the theoretical value); the Mg-O content was 2.19 weight percent (theory=2.28). The precipitate weighed less than 1 g. Diethylether could no longer be shown present in the solution.

The bright brown 26.33 percent solution was storage stable for three months. Also a solution concentrated to 60 percent remained storage stable.

The concentrated product crystallized after several days at 20° C. Nevertheless, it could be easily liquefied by dipping into a bath heated to about 50° C.

EXAMPLES 3–9

3. BuEtMg (complexed with 1/37 mol of Bu₃Al) with Mg(OsBu)₂.
   Viscosity: 80 centiStokes at 20° C.; $d^{20}=0.93$ g cm$^{-3}$.

4. nHex₂Mg (complexed with 1/37 mol of Et₃Al) with Mg(OEt) elemental analysis: C=63.4% (theory=62.22%); H=12.04% (11.67%); Mg=14.97% (15.75%).

5. nOc₂Mg (complexed with 1/20 mol of THF) with Mg(OEt)₂, elemental analysis: C=66.5% (theory=65.83%); H=12.59% (12.07%); Mg=13.0 (13.33%).

6. BuOcMg (complexed with 1/40 Mol Bu₃Al) with Mg(OiPr)₂+Mg(OEt)₂(1:1),
   elemental analysis: Mg=14.67% (theory=15.07%); after decomposition, a mol ratio of isopropanol to ethanol of 1:0.923 was found (gas chromatographically, injection method).

7. Bu₁.₅Oc₀.₅Mg [complexed with 1/45 mol of Al-(OiPr)₃]with Mg(OEt)₂ in a mol ratio of 2:1,
   elemental analysis: C=65.54% (theory 64.44%); Mg=15.97% (16.31%).

8. Ph₂Mg (complexed with 1/25 mol Et₃At) with Mg(OtBu)₂,
   elemental analysis: Mg=13.75% (theory 13.94%); integration of the NMR-spectrum gave a ratio of the phenyl protons to the t-butyl protons of 5:8.6 (theory=5:9).

9. BusBuMg (not-complexed) in an 8% solution of iso-octane with Mg(OiPr)₂, viscosity of the concentrate: 67 centiStokes at 23° C.; $d^{20}=0.91$ g cm$^{-3}$.

The concentrates of Examples 4 and 5 were waxy or oily of high viscosity. All the others were readily mobile oils.

10. Preparation of Bu₀.₇₅Oc₀.₂₅Mg(OEt)₀.₈(OiPr)₀.₂
    217.4 g of a 15.3% toluene solution of Bu₁.₅Oc₀.₅Mg (0.20 mol; complexed with 1/37 mol of Al-isopropylate per mol of R₂Mg) were combined with 18.28 g of magnesium ethylate (0.16 mol) and 5.7 g of magnesium di-isopropylate (0.04 mol) and kept at boiling temperature for one hour. Everything dissolved.

After removal of the solvent, an oil remained which showed no tendency toward crystallization after six weeks' storage at about 15° C.

After decomposition with diluted hydrochloric acid, a mol ratio of i-propanol to ethanol of 1:3.99 was determined (gas chromatographically, injection method).

Solubility Data

Bu₀.₇₅Oc₀.₂₅Mg(OEt)₀.₈(OiPr)₀.₂ (Example 10) is miscible in all proportions with hexane, nonane, toluene, and diethylether.

Bu₀.₇₅Oc₀.₂₅Mg(OEt) (Example 2) is, when warmed, completely miscible in all proportions with hexane, nonane, toluene, and diethylether. After standing for several days, solutions of a concentration of more than 60% in hexane and nonane completely crystallize; solutions at a concentration of 60% or lower percentage are storage stable. In toluene, this limit stands at about 70%. Even 90% solutions do not crystallize out of diethylether.

Bu₀.₅s-Bu₀.₅Mg(OiPr) (Example 9) is completely miscible in all proportions in the aforementioned solvents.

PhMg(OtBu) (Example 8) dissolves in the aforementioned solvents to form a clear solution (80%) when heated. In hexane and nonane, the solutions become cloudy after standing for several days at about 20° C. 50% solutions in hexane and nonane remain clear.

Comparison Example:

6.04 g of t-butyl alcohol (81.5 mMol) were added dropwise to a solution of diethylmagnesium in diethylether (content: 40.75 mMol in 35 g of solution), while cooling to 0° C. After warming to room temperature (about 25° C.), the batch was stirred for one-half hour and again 35 g of ethereal diethylmagnesium solution were added. The batch was stirred for 6 hours under reflux (36° C.). The precipitate was then filtered off and identified as Mg(OtBu)₂. It weighed 6.94 g. In the first step of the reaction, 6.94 g of Mg(OtBu)₂ could have been formed: i.e. the reaction forming ethylmagnesium-t-butylate had not taken place.

A product prepared according to the method of the invention was soluble in ether to form a clear solution.

What is claimed is:

1. A method for making an organomagnesium alkoxide, free of halogen and soluble in hydrocarbons, of the formula $$R^1{}_aR^2{}_bMg(OR^3)_c(OR^4)_d$$

wherein R¹ and R² are the same or different and are phenyl or alkyl having 1 to 12 carbon atoms, R³ and R⁴ are the same or different and are alkyl having 2 to 6 carbon atoms, and wherein (a+b) and (c+d) are both equal to 1, which method comprises reacting a reagent consisting essentially of a hydrocarbon-soluble diorganomagnesium compound of the formula $$(R^1{}_aR^2{}_b)_2Mg$$

at a temperature from about 50° C. to about 160° C. with a compound of the formula $$Mg[(OR^3)_c(OR^4)_d]_2$$

in an ether-free inert hydrocarbon solvent.

2. A method as in claim 1 wherein the reaction temperature is from about 80° C. to about 120° C.

3. A method as in claim 1 wherein R¹ is butyl and R² is octyl.

4. A method as in claim 3 wherein R³ and R⁴ are selected from the group consisting of ethyl and isopropyl.

* * * * *

UNITED STATES PATENT AND TRADEMARK OFFICE
CERTIFICATE OF CORRECTION

PATENT NO. : 4,410,742
DATED : October 18, 1983
INVENTOR(S) : Schroeer et al.

It is certified that error appears in the above-identified patent and that said Letters Patent is hereby corrected as shown below:

On the face of the patent, line designation "75 Inventor:", add -- Ulrich Schroeer, Kamen-Methler -- after "Werne"; and line designation "73 Assignees:", delete "Ulrich Schroeer, Kamen-Methler".

Column 1, lines 19 and 20, this reaction should appear on a single line, i.e. as -- $2\ RCl + 2\ Mg + R'OH \longrightarrow R\text{-}Mg\text{-}OR' + MgCl_2 + RH$ --

Column 1, line 46, replace "difficulty" by -- difficultly --.

Signed and Sealed this

Twenty-ninth Day of January 1985

[SEAL]

Attest:

DONALD J. QUIGG

Attesting Officer     Acting Commissioner of Patents and Trademarks